(12) United States Patent
    Prefontaine

(10) Patent No.:     US 12,649,698 B2
(45) Date of Patent:          Jun. 9, 2026

(54) SYSTEM FOR PRODUCING AGGLOMERATED ORGANIC MICROBIAL FERTILIZER

(71) Applicant: Earth Medicine LLC., Burley, ID (US)

(72) Inventor: Daniel Prefontaine, Albion, ID (US)

(73) Assignee: Earth Medicine LLC., Burley, ID (US)

( * ) Notice:      Subject to any disclaimer, the term of this patent is extended or adjusted under 35 U.S.C. 154(b) by 82 days.

(21) Appl. No.: 18/900,709

(22) Filed:      Sep. 28, 2024

(65)              Prior Publication Data
    US 2026/0092020 A1      Apr. 2, 2026

(51) Int. Cl.
    *C05F 3/06*          (2006.01)
    *C05F 5/00*          (2006.01)
    *C12N 1/20*          (2006.01)
(52) U.S. Cl.
    CPC ................ *C05F 3/06* (2013.01); *C05F 5/002* (2013.01); *C12N 1/20* (2013.01)
(58) Field of Classification Search
    CPC ............... C05F 3/06; C05F 5/002; C12N 1/20
    See application file for complete search history.

(56)              References Cited

U.S. PATENT DOCUMENTS

| | | | |
|---|---|---|---|
| 4,062,641 A | * | 12/1977 | Hovmand ............... A23P 10/22 425/222 |
| 5,451,523 A | * | 9/1995 | Von Fahnestock ..... C05F 17/90 435/286.7 |
| 2006/0101881 A1 | * | 5/2006 | Carin ........................ C05F 3/00 71/21 |

* cited by examiner

*Primary Examiner* — James Sanders
(74) *Attorney, Agent, or Firm* — Hawley Troxell; Philip McKay

(57)              ABSTRACT

A system for providing agglomerated bovine-based organic microbial fertilizer utilizes a novel agglomeration system to produce agglomerated bovine-based organic microbial fertilizer composed of generally spherical granules that have a high density of nutrients per volume, have almost no odor, and have a shelf life of years when properly packaged and stored, can be sized such that industry standard equipment and spreaders can be used to apply the resulting agglomerated bovine-based organic microbial fertilizer, and can be sized to accommodate various types of uses including residential and commercial uses.

15 Claims, 12 Drawing Sheets

299

SYSTEM FOR PRODUCING AGGLOMERATED ORGANIC MICROBIAL FERTILIZER

BACKGROUND

Over the years, a number of different types of fertilizer compositions have been developed and employed in agriculture. In the recent past, synthetic chemical fertilizer compositions dominated the fertilizer marketplace. However, more recently, there has been increasing public awareness of, and concern regarding, the potential link between synthetic chemical fertilizer use and human disease and/or poisoning. Consequently, there has been a significant movement toward "organic" fertilizers and organic fertilizer compositions which do not rely on synthetic chemicals and which are typically derived from natural sources.

As a result of the increased demand for organic fertilizer compositions, there is significant interest in the development of new and/or better organic fertilizers and compositions that provide the desirable and/or necessary nutrients and organic fertilizer compositions that are easily stored and can easily be applied where needed.

One particularly effective and desirable form of organic fertilizer is microbial organic fertilizer. While a highly desirable and effective organic fertilizer, prior art organic microbial fertilizer is typically relatively low density in terms of volume per desired nutrients provided.

This low density of prior art organic microbial fertilizer means that large volumes of prior art organic microbial fertilizer are needed to effectively fertilize. This, in turn, creates often unacceptable transportation and storage issues. In addition, prior art organic microbial fertilizer typically has very short storage life, i.e., once composted it must be used relatively immediately.

Another issue with prior art organic microbial fertilizer is that prior art organic microbial fertilizers typically have a very strong odor that can remain not only during storage, but long after the prior art organic microbial fertilizer is applied. This makes prior art organic microbial fertilizer problematic for residential use and commercial uses where people are around prior art organic microbial fertilizer.

In addition, because of the low density of prior art organic microbial fertilizer, prior art organic microbial fertilizer cannot be readily applied using conventional spreaders and/or traditional application methods. Consequently, prior art organic microbial fertilizer typically must be applied by special methods and equipment, thereby raising the effective cost of using prior art organic microbial fertilizer.

As result of these and other issues, prior art organic microbial fertilizer is typically not viewed as the organic fertilizer of first choice, despite the known advantages of its use as an organic fertilizer.

What is needed is a method and system for providing organic microbial fertilizer that has a high density of nutrients per volume, does not have significant odor, has a relatively long shelf-life, can be applied using standard application equipment, and can be processed to accommodate various types of use including residential and commercial.

SUMMARY

Disclosed herein is a method and system for providing organic microbial fertilizer that has a high density of nutrients per volume, does not have significant odor, has a relatively long shelf-life, can be applied using standard application equipment, and can be processed to accommodate various types of uses including residential and commercial.

To this end, disclosed herein is a method and system for providing agglomerated bovine-based organic microbial fertilizer that utilizes a novel agglomeration system to produce agglomerated bovine-based organic microbial fertilizer composed of generally spherical granules that have a high density of nutrients per volume, have almost no odor, and have a shelf life of years when properly packaged and stored.

In addition, by controlling the average size of the grains of the agglomerated bovine-based organic microbial fertilizer produced using the disclosed methods and systems, the agglomerated bovine-based organic microbial fertilizer can be sized such that industry standard equipment and spreaders can be used to apply the resulting agglomerated bovine-based organic microbial fertilizer.

In addition, using the disclosed methods and systems, the average size of the grains of the resulting agglomerated bovine-based organic microbial fertilizer can be manipulated to accommodate various types of uses including residential and commercial uses.

In one embodiment, the agglomeration system includes an agglomeration chamber, the agglomeration chamber having an agglomeration chamber exterior surface and an agglomeration chamber interior space with an agglomeration chamber interior surface.

In one embodiment, the agglomeration system includes an agglomeration chamber rotational drive system for selectively rotating the agglomeration chamber.

In one embodiment, the agglomeration system includes an agglomeration chamber misting system for selectively providing a mist of water to the interior space of the agglomeration chamber.

In one embodiment, the agglomeration system includes an agglomeration system air flow system for providing air to the agglomeration system.

In one embodiment, the agglomeration system includes an agglomeration chamber dryer for selective applying heat to the interior space of the agglomeration chamber.

In one embodiment, the agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the agglomeration system includes an agglomeration chamber thermal isolation housing heating system for selectively applying heat to the agglomeration chamber thermal isolation housing.

In one embodiment, a method for producing organic microbial fertilizer is disclosed that utilizes the disclosed agglomeration system.

In one embodiment, the method includes providing composted bovine-based organic material.

In one embodiment, a screening of composted bovine-based organic material is performed to generate screened composted bovine-based organic material.

In one embodiment, the disclosed agglomeration system is provided. In one embodiment, the agglomeration system includes an agglomeration chamber. In one embodiment, the agglomeration chamber has an agglomeration chamber exterior surface and an agglomeration chamber interior space with an agglomeration chamber interior surface.

In one embodiment, the agglomeration system includes an agglomeration chamber rotation drive system for selectively rotating the agglomeration chamber.

In one embodiment, the agglomeration system includes an agglomeration chamber misting system for selectively providing a mist of water to the interior space of the agglomeration chamber.

In one embodiment, the agglomeration system includes an agglomeration system air flow system for providing air to the agglomeration system.

In one embodiment, the agglomeration system includes an agglomeration chamber dryer for selectively applying heat to the interior space of the agglomeration chamber.

In one embodiment, the agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the agglomeration system includes an agglomeration chamber thermal isolation housing heating system for selectively applying heat to an agglomeration chamber thermal isolation housing interior space.

In one embodiment, the screened composted bovine-based organic material is provided to the interior space of agglomeration chamber.

In one embodiment, the screened composted bovine-based organic material in the interior space of agglomeration chamber is agglomerated to generate agglomerated bovine-based organic material.

In one embodiment, the screened composted bovine-based organic material in the interior space of agglomeration chamber is agglomerated to generate agglomerated bovine-based organic material by using the agglomeration chamber rotational drive system to rotate the agglomeration chamber and the screened composted bovine-based organic material inside the interior space of agglomeration chamber.

In one embodiment, the screened composted bovine-based organic material in the interior space of agglomeration chamber is agglomerated to generate agglomerated bovine-based organic material by using the agglomeration chamber misting system to provide a mist of water to the interior space of agglomeration chamber and the screened composted bovine-based organic material in the interior space of agglomeration chamber as the agglomeration chamber is rotated by the agglomeration chamber rotational drive system.

In one embodiment, the screened composted bovine-based organic material in the interior space of agglomeration chamber is agglomerated to generate agglomerated bovine-based organic material by using the agglomeration chamber thermal isolation housing heating system to heat the agglomeration chamber thermal isolation housing interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system.

In one embodiment, as the agglomeration chamber is concurrently rotated by the agglomeration chamber rotational drive system, misted by the agglomeration chamber misting system, and the agglomeration chamber interior surface of the agglomeration chamber interior space is maintained at the desired temperature, as the screened composted bovine-based organic material is being agglomerated, the grain size of the agglomerated bovine-based organic material is monitored.

In one embodiment, when a desired average grain size of the agglomerated bovine-based organic material is achieved, the agglomeration chamber misting system is turned off and the agglomeration chamber dryer is activated to apply heat to the agglomeration chamber interior space to dry the agglomerated bovine-based organic material in the agglomeration chamber interior space.

In one embodiment, a moisture content of the agglomerated bovine-based organic material is monitored as the agglomerated bovine-based organic material is being dried.

In one embodiment, when a desired moisture content of the agglomerated bovine-based organic material is achieved, the agglomeration chamber thermal isolation housing heating system and the agglomeration chamber dryer are turned off. Then the agglomeration system air flow system either remains on, or is turned on, so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, a screening of the cooled agglomerated bovine-based organic material is performed to generate agglomerated bovine-based organic microbial fertilizer.

When the disclosed methods and systems are utilized, the resulting agglomerated bovine-based organic microbial fertilizer is composed of generally spherical granules that have a high density of nutrients per volume. In addition, the resulting agglomerated bovine-based organic microbial fertilizer has almost no odor and, when packaged and stored correctly, has a shelf life of years.

In addition, by controlling the average size of the grains of the agglomerated bovine-based organic microbial fertilizer produced using the disclosed methods and systems, the agglomerated bovine-based organic microbial fertilizer can be sized such that industry standard equipment and spreaders can be used to apply the resulting agglomerated bovine-based organic microbial fertilizer.

In addition, using the disclosed methods and systems, the average size of the grains of the resulting agglomerated bovine-based organic microbial fertilizer can be manipulated to accommodate various types of uses including residential and commercial uses.

Therefore, as discussed in more detail below, the disclosed methods and systems address the shortcomings of the prior art by providing a technical solution to the long standing technical problem of providing organic microbial fertilizer that has a high density of nutrients per volume, does not have significant odor, has a relatively long shelf-life, can be applied using standard application equipment, and can be processed to accommodate various types of uses including residential and commercial.

Figure 1A:
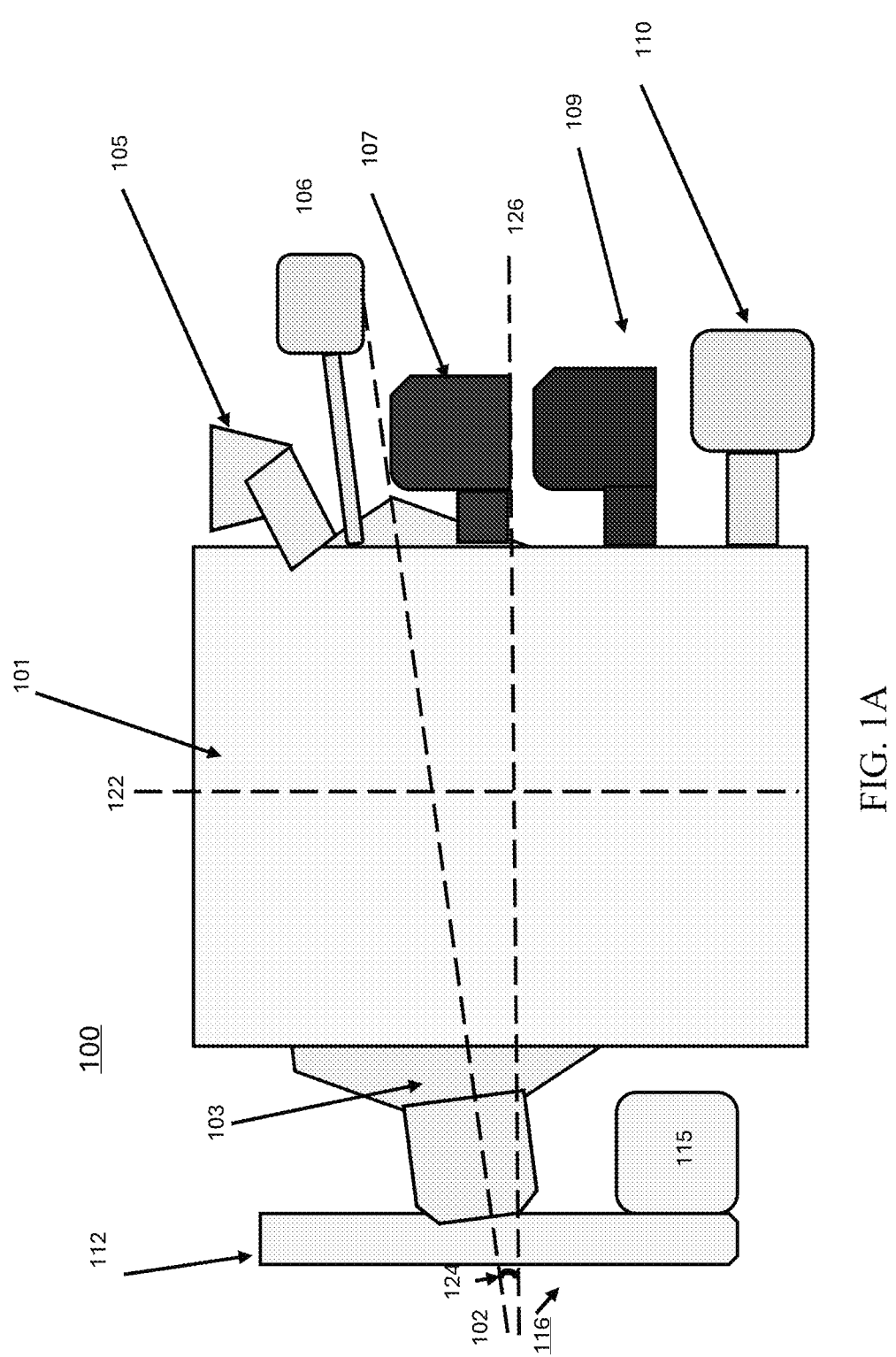
FIG. 1A shows a side view of a specific illustrative example of an agglomeration system in accordance with one embodiment.

Common reference numerals are used throughout the figures and the detailed description to indicate like elements. One skilled in the art will readily recognize that the above figures are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying figures (FIGs.), which depict one or more exemplary embodiments. Embodiments may be implemented in many different forms and should not be construed as limited to the embodiments set forth herein, shown in the FIGs., and/or described below. Rather, these exemplary embodiments are provided to allow a complete disclosure that conveys the principles of the invention, as set forth in the claims, to those of skill in the art.

Disclosed herein is a method and system for providing organic microbial fertilizer that has a high density of nutrients per volume, does not have significant odor, has a relatively long shelf-life, can be applied using standard application equipment, and can be processed to accommodate various types of uses including residential and commercial.

Agglomeration System

To this end, disclosed herein is a method and system for providing agglomerated bovine-based organic microbial fertilizer that utilizes a novel agglomeration system to produce agglomerated bovine-based organic microbial fertilizer composed of generally spherical granules that have a high density of nutrients per volume, have almost no odor, and have a shelf life of years when properly packaged and stored.

Figure 1B:
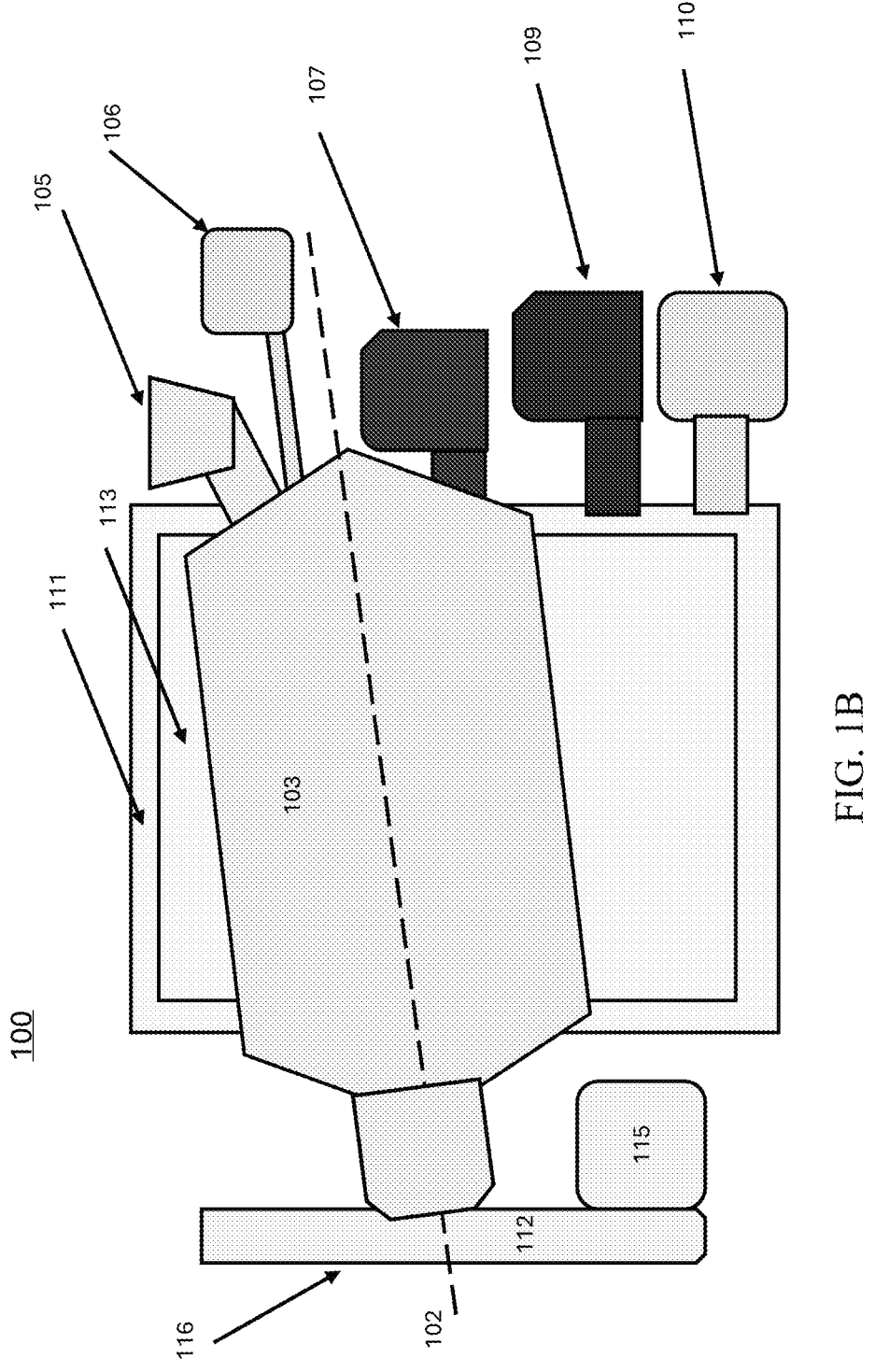
FIG. 1B shows a side view of the specific illustrative example of an agglomeration system of FIG. 1A in partial cutaway in accordance with one embodiment.
Figure 1C:
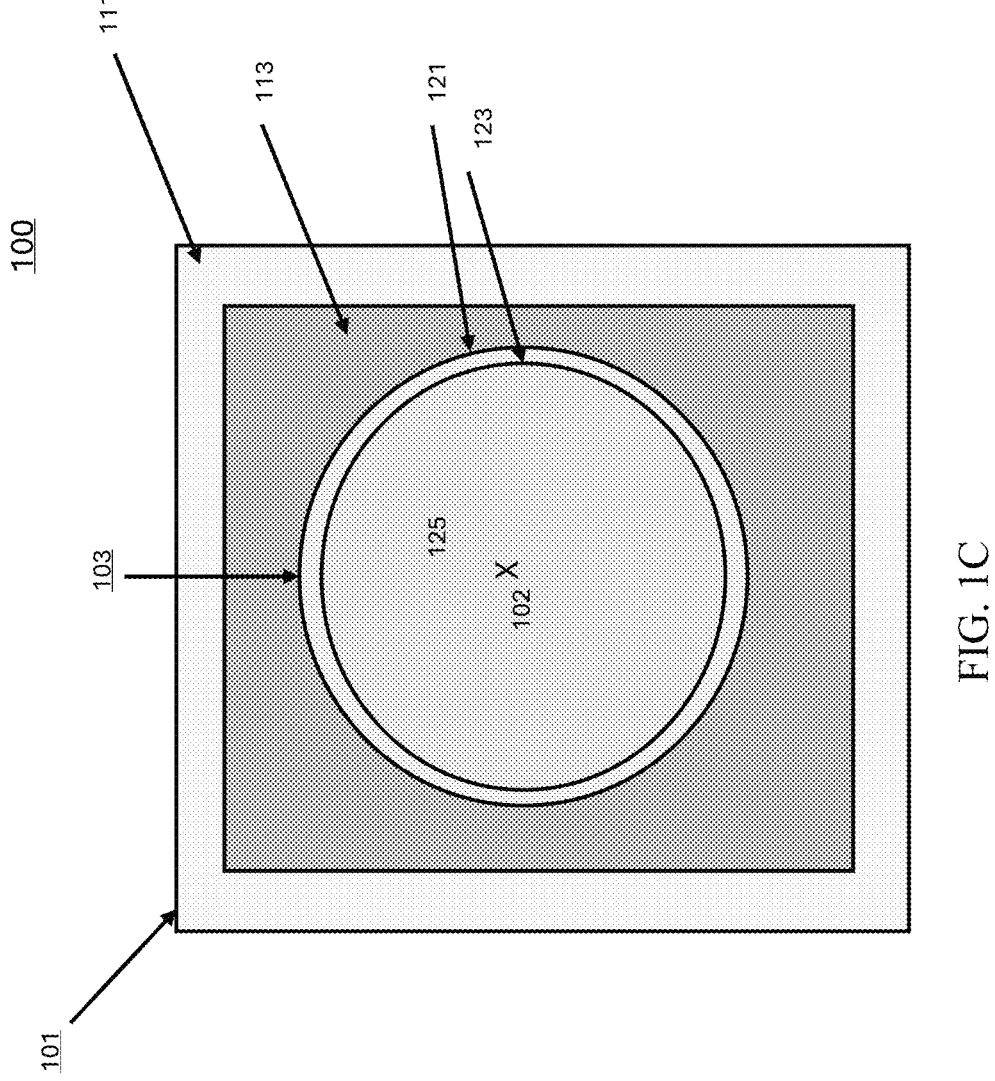
FIG. 1C shows an end view of the specific illustrative example of an agglomeration system of FIGS. 1A and 1B in cutaway in accordance with one embodiment.

FIG. 1A shows a side view of a specific illustrative example of the disclosed agglomeration system 100 in accordance with one embodiment. FIG. 1B shows a side view of the agglomeration system 100 of FIG. 1A in partial cutaway in accordance with one embodiment. FIG. 1C shows an end view of the agglomeration system 100 of FIGS. 1A and 1B as cutaway along line 122 of FIG. 1A in accordance with one embodiment.

Referring to FIGS. 1A, 1B and 1C together, in one embodiment, agglomeration system 100 includes an agglomeration chamber thermal isolation housing 101, and an agglomeration chamber 103.

As seen in FIG. 1A, in one embodiment, agglomeration chamber thermal isolation housing 101 encloses at least a portion of agglomeration chamber 103 and thereby thermally isolates at least a portion of agglomeration chamber 103. In one embodiment, agglomeration chamber 103 is free to rotate around agglomeration chamber centerline axis 102 while enclosed in agglomeration chamber thermal isolation housing 101 under the power of agglomeration chamber rotational drive system 116.

FIG. 1B shows agglomeration system 100 with half of agglomeration chamber thermal isolation housing 101 cut away to expose the entirety of agglomeration chamber 103, including the portion enclosed by agglomeration chamber thermal isolation housing 101.

In various embodiments, agglomeration chamber 103 can be made of steel, or any metal, or any alloy or material that is capable of conducting thermal energy, as discussed herein, and/or as known in the art at the time of filing, and/or as made known or available after the time of filing.

Referring to FIG. 1C, in one embodiment, agglomeration chamber 103 has an agglomeration chamber exterior surface 121 and an agglomeration chamber interior space 125 with an agglomeration chamber interior surface 123.

In the specific illustrative example of FIGS. 1A, 1B, and 1C, agglomeration chamber 103 is positioned such that agglomeration chamber centerline axis 102 is at an illustrative angle 124 with respect to level line 126. However, those of skill in the art will recognize that angle 124 can any angle desired ranging from zero to ninety degrees as desired.

In one various embodiments, agglomeration chamber thermal isolation housing 101 includes agglomeration chamber thermal isolation housing walls 111 (see FIG. 1C) that enclose an agglomeration chamber thermal isolation housing thermally isolated interior space 113 that, in turn, is in thermal contact with agglomeration chamber exterior surface 121.

In one embodiment, agglomeration chamber thermal isolation housing 101 is constructed of metal, fiber glass, ceramic material, and/or any combination of materials that serve to provide thermal isolation of agglomeration chamber thermal isolation housing thermally isolated interior space 113 and can enclose at least a portion of agglomeration chamber 103, as discussed herein, and/or as known in the art at the time of filing, and/or as becomes available after the time of filing.

Referring to FIGS. 1A, 1B, and 1C together, agglomeration system 100 further includes an input opening/hopper 105. As discussed in more detail below, in one embodiment, input opening/hopper 105 is used to provide bovine-based organic material into agglomeration chamber interior space 125 of agglomeration chamber 103 and to remove the resultant agglomerated bovine-based organic microbial fertilizer produced.

In one embodiment, agglomeration system 100 includes agglomeration chamber misting system 106. As discussed below, agglomeration chamber misting system 106 is used to provide a mist of water to agglomeration chamber interior space 125 of agglomeration chamber 103 during various stages of the processing of bovine-based organic material into the resultant agglomerated bovine-based organic microbial fertilizer.

Misting systems are well known in the art. Therefore, a more detailed discussion of the type and operation of agglomeration chamber misting system 106 is omitted here to avoid detracting from the invention. In various embodiments, agglomeration chamber misting system 106 can be any misting system capable of providing a liquid mist to agglomeration chamber interior space 125 of agglomeration chamber 103 during various stages of the processing as discussed herein, and/or as known in the art at the time of filing, and/or as becomes available after the time of filing.

In one embodiment, agglomeration system 100 includes an agglomeration chamber dryer 107. As discussed below, agglomeration chamber dryer 107 is used to selectively provide heat to agglomeration chamber interior space 125 of agglomeration chamber 103 during the drying stages of the processing of bovine-based organic material into the resultant agglomerated bovine-based organic microbial fertilizer.

In various embodiments, agglomeration chamber dryer 107 can be any one of numerous types of heat source systems known in the art. Dryers and heat source systems are well known in the art. Therefore a more detailed discussion of the type and operation of agglomeration chamber dryer 107 is omitted here to avoid detracting from the invention.

In one embodiment, agglomeration system 100 includes agglomeration chamber thermal isolation housing heating system 109. In one embodiment, agglomeration chamber thermal isolation housing heating system 109 selectively provides heat to agglomeration chamber thermal isolation housing 101.

As discussed below, the heat provided by agglomeration chamber thermal isolation housing heating system 109 is used to heat the agglomeration chamber thermal isolation housing thermally isolated interior space 113 of agglomeration chamber thermal isolation housing 101 that, in turn, is in thermal contact with agglomeration chamber exterior surface 121 (see FIG. 1C). Thus, in one embodiment, agglomeration chamber thermal isolation housing heating system 109 is used to heat agglomeration chamber exterior surface 121, and thereby heat agglomeration chamber interior surface 123, to a desired temperature and to maintain heat agglomeration chamber interior surface 123 at the desired temperature during the agglomeration process.

In various embodiments, agglomeration chamber thermal isolation housing heating system 109 can be any one of numerous types of heat source systems known in the art. Heat source systems are well known in the art. Therefore, a more detailed discussion of the type and operation of agglomeration chamber thermal isolation housing heating system 109 is omitted here to avoid detracting from the invention.

In one embodiment, agglomeration system 100 includes agglomeration system air flow system 110. As discussed below, in one embodiment, agglomeration system air flow system 110 is used to provide forced outside air into agglomeration chamber thermal isolation housing thermally isolated interior space 113 to relatively rapidly cool agglomeration chamber thermal isolation housing thermally isolated interior space 113 of agglomeration chamber thermal isolation housing 101 when a desired moisture content of the agglomerated bovine-based organic material is achieved.

In various embodiments, agglomeration system air flow system 110 can be any one of numerous types of forced air systems or fans known in the art. Forced air/fan systems are well known in the art. Therefore, a more detailed discussion of the type and operation of agglomeration system air flow system 110 is omitted here to avoid detracting from the invention.

In one embodiment, agglomeration system 100 includes agglomeration chamber rotational drive system 116. In one embodiment, agglomeration chamber 103 is free to rotate around agglomeration chamber centerline axis 102 while enclosed in agglomeration chamber thermal isolation housing 101 under the power of agglomeration chamber rotational drive system 116.

Numerous types of agglomeration chamber rotational drive systems 116 can be used. In the specific example of FIGS. 1A. 1B. and 1C, agglomeration chamber rotational drive system 116 includes an agglomeration chamber rotational drive system motor 115 and a chain drive 112.

Rotational drive systems are well known in the art. Therefore a more detailed discussion of the type and operation of agglomeration chamber rotational drive system 116 is omitted here to avoid detracting from the invention.

Figure 1D:
FIG. 1D is a perspective a first end view of a specific illustrative example of an agglomeration system in accordance with one embodiment.

FIG. 1D is a perspective first end view of a specific illustrative example of an agglomeration system, such as agglomeration system 100 in accordance with one embodiment.

Figure 1E:
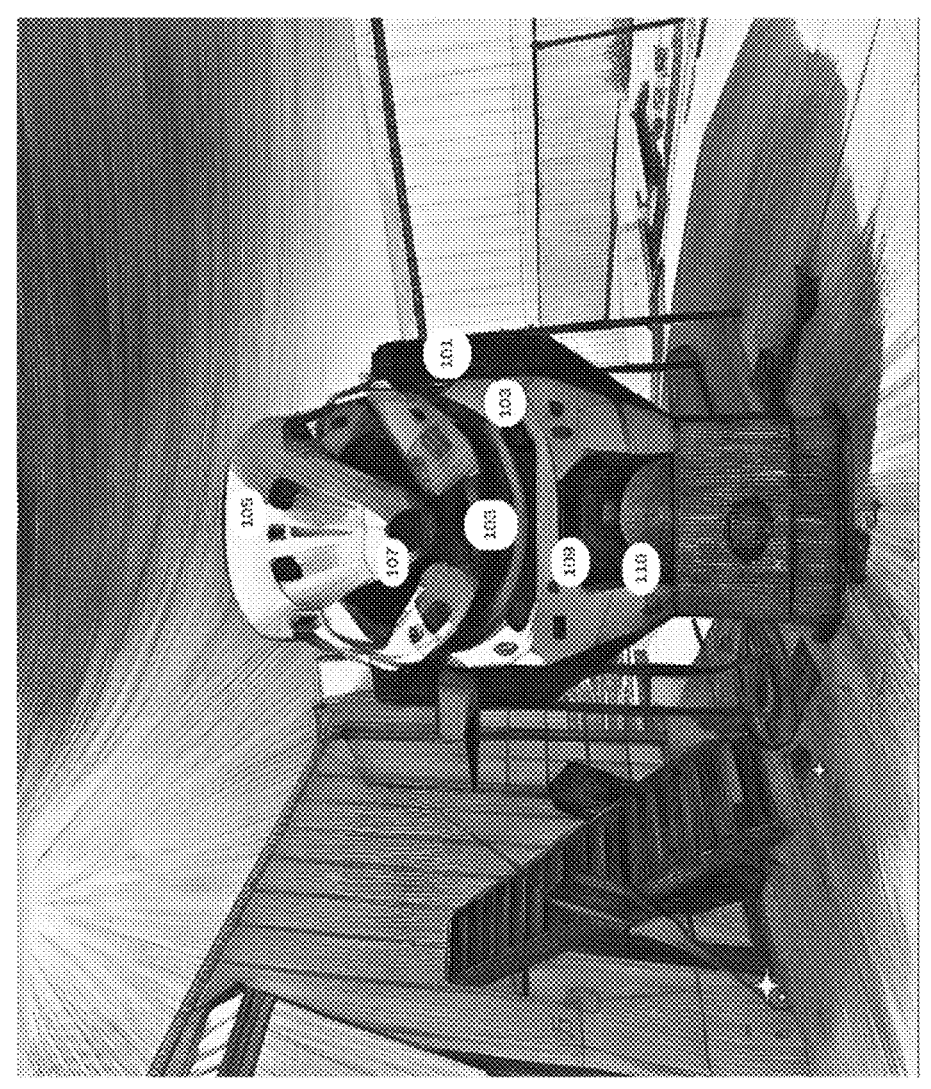
FIG. 1E is a first end view of a specific illustrative example of an agglomeration system in accordance with one embodiment.

FIG. 1E is a first end view of a specific illustrative example of an agglomeration system, such as agglomeration system 100 in accordance with one embodiment.

Figure 1F:
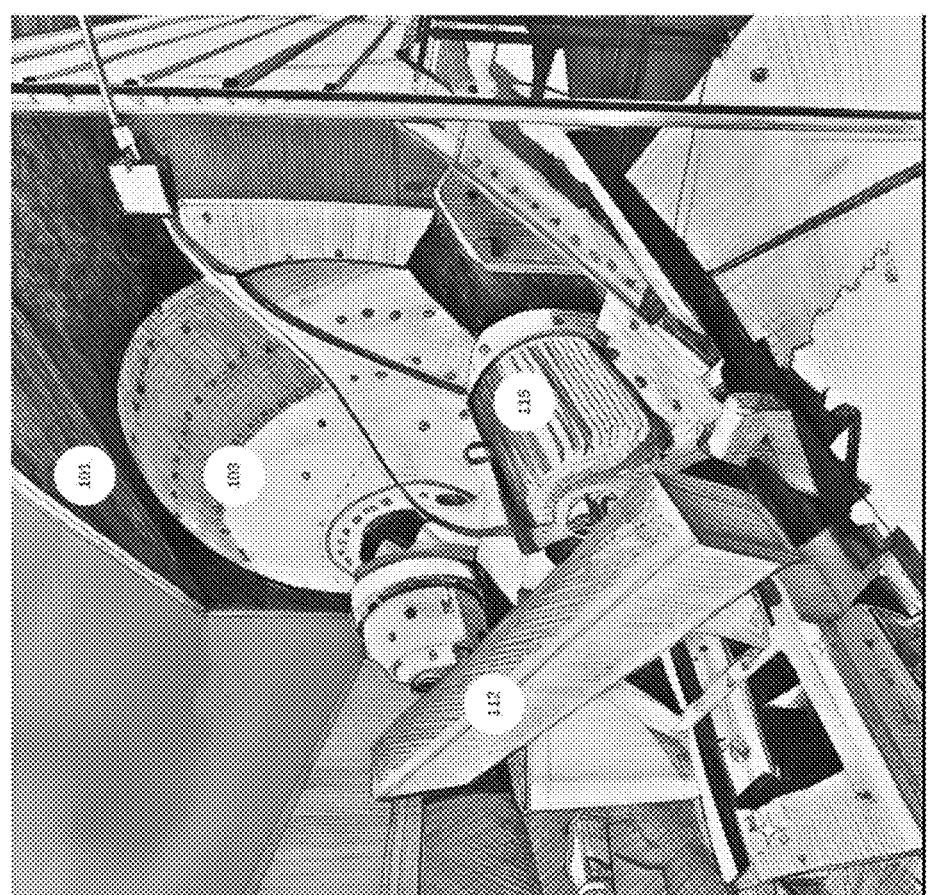
FIG. 1F is a perspective second end view of a specific illustrative example of an agglomeration system in accordance with one embodiment.

FIG. 1F is a perspective second end view of a specific illustrative example of an agglomeration system, such as agglomeration system 100 in accordance with one embodiment.

Process

Disclosed herein is a process for producing agglomerated organic microbial fertilizer that, in one embodiment, utilizes the disclosed agglomeration system, such as agglomeration system 100 of FIGS. 1A through 1F discussed above.

Figure 2A:
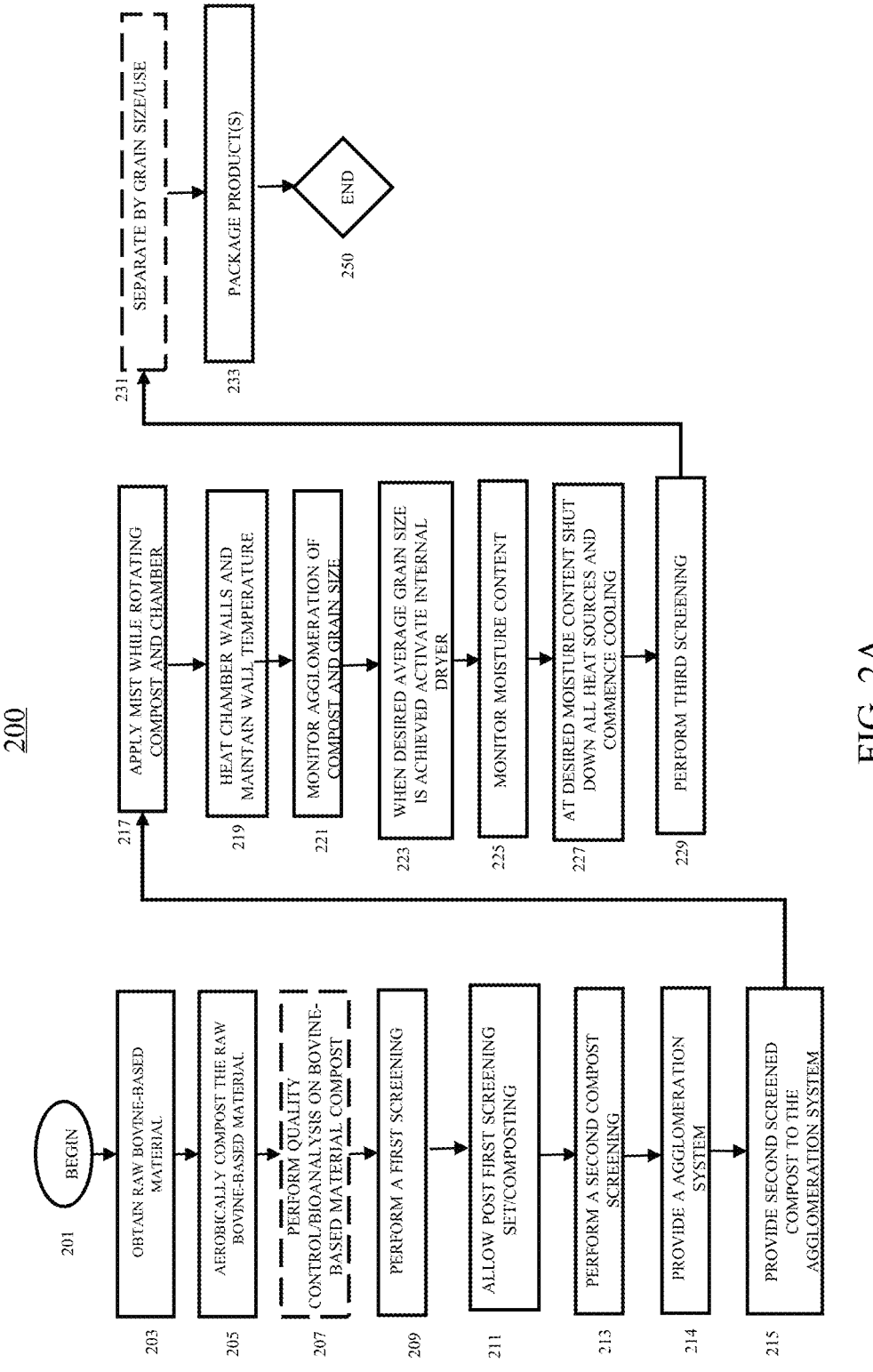
FIG. 2A is a flow chart of a process for producing agglomerated organic microbial fertilizer in accordance with one embodiment.

FIG. 2A is a flow chart of a process 200 for producing agglomerated organic microbial fertilizer in accordance with one embodiment.

Figure 2B:
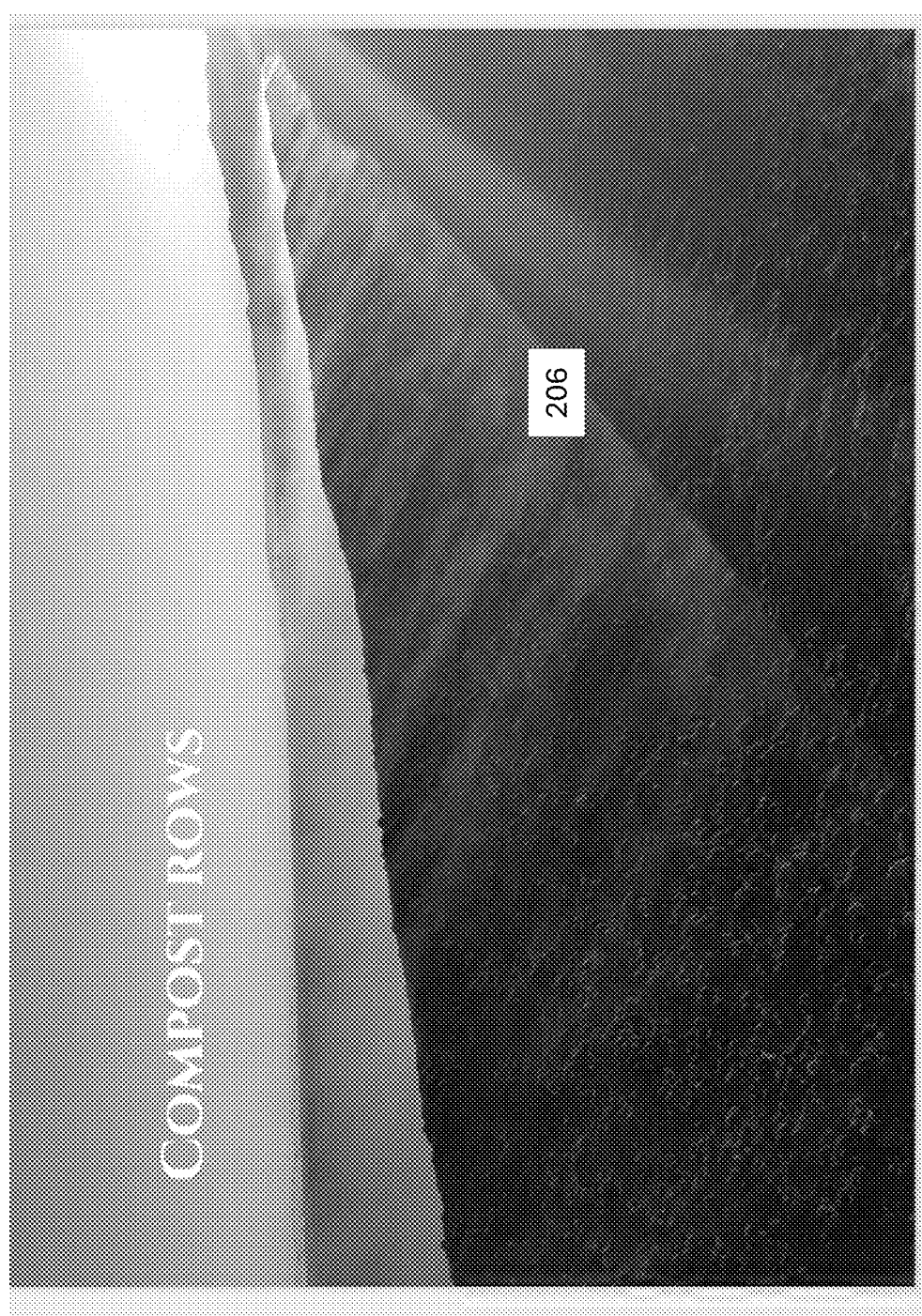
FIG. 2B shows raw bovine-based organic material used in the process for producing agglomerated organic microbial fertilizer of FIG. 2A in accordance with one embodiment.

FIG. 2B shows raw bovine-based organic material used in the process 200 for producing agglomerated organic microbial fertilizer of FIG. 2A in accordance with one embodiment.

Figure 2C:
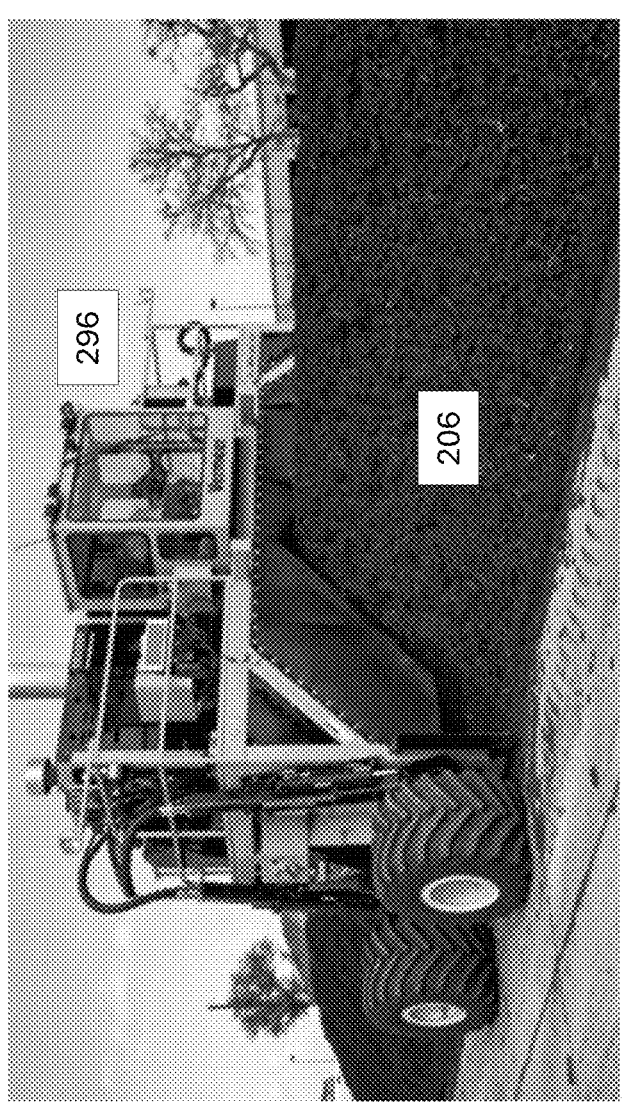
FIG. 2C shows the turning of raw bovine-based organic material of FIG. 2B during composting used in the process for producing agglomerated organic microbial fertilizer of FIG. 2A in accordance with one embodiment.

FIG. 2C shows the turning of raw bovine-based organic material of FIG. 2B during composting of the raw bovine-based organic material used in the process 200 for producing agglomerated organic microbial fertilizer of FIG. 2A in accordance with one embodiment.

Figure 2D:
FIG. 2D shows a screening of the settled composted bovine-based organic material and providing the screened composted bovine-based organic material to the disclosed agglomeration system during the process for producing agglomerated organic microbial fertilizer of FIG. 2A in accordance with one embodiment.

FIG. 2D shows screening of the settled composted bovine-based organic material and providing the second screened composted bovine-based organic material to the disclosed agglomeration system during the process 200 for producing agglomerated organic microbial fertilizer of FIG. 2A in accordance with one embodiment.

Figure 2E:
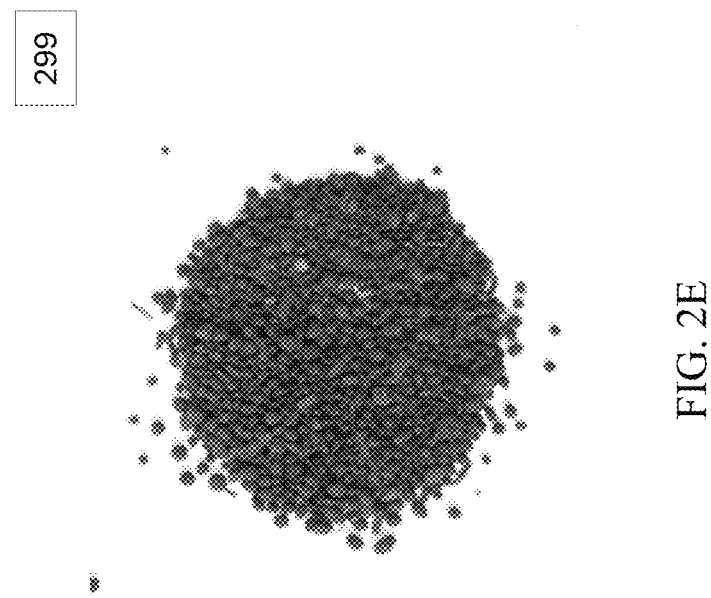
FIG. 2E shows one specific example of the agglomerated bovine-based organic microbial fertilizer produced using the process for producing agglomerated organic microbial fertilizer of FIG. 2A in accordance with one embodiment.

FIG. 2E shows one specific example of the agglomerated bovine-based organic microbial fertilizer produced using the process 200 for producing agglomerated organic microbial fertilizer of FIG. 2A in accordance with one embodiment.

One specific illustrative example of one embodiment of the disclosed method for producing agglomerated organic microbial fertilizer will now be discussed with reference FIGS. 1A through 1F and FIGS. 2A, through 2E together.

Referring to FIG. 2A, in one embodiment, process 200 begins at operation 201 and process flow proceeds to operation 203.

In one embodiment, at operation 203 raw bovine-based organic material is obtained.

In various embodiments, the raw bovine-based organic material obtained at operation 203 includes material from pens holding cattle. Therefore, the raw bovine-based organic material obtained at operation 203 can include bovine feces, straw or other bedding, and bovine food from the floor of the cattle pens.

In one embodiment, the raw bovine-based organic material obtained at operation 203 includes material from pens holding dairy cows. Therefore, the raw bovine-based organic material obtained at operation 203 can include dairy cow feces, straw or other bedding, and food from the floor of the dairy cow pens.

In one embodiment, the raw bovine-based organic material obtained at operation 203 is put into rows such as raw bovine-based organic material row 206 of FIG. 2B.

In various embodiments, raw bovine-based organic material row 206 is of a generally trapezoidal shape having a ten to twenty foot base width and a height of five to ten feet. In one embodiment, raw bovine-based organic material row 206 has a sixteen foot base and a height of eight feet. In other embodiments, raw bovine-based organic material row 206 can be of any shape and dimensions desired.

In one embodiment, once raw bovine-based organic material is obtained at operation 203, process flow proceeds to operation 205.

In one embodiment, at operation 205 an initial composting of the raw bovine-based organic material of operation 203 is performed to generate composted bovine-based organic material.

In one embodiment, at operation 205 the raw bovine-based organic material of operation 203 is aerobically composted until the temperature of the bovine-based organic material becomes stable at a temperature of one hundred and sixty degrees Fahrenheit or less and a moisture level of thirty five to sixty percent is achieved.

In various embodiments, the initial composting of the raw bovine-based organic material takes up to ninety days or more with the composting bovine-based organic material being checked every five to ten days to ensure the temperature remains below one hundred and sixty degrees Fahrenheit and has a moisture level of thirty five percent or more.

In addition, in one embodiment, as the bovine-based organic material is composted, it is turned every five to ten days to allow oxygen to contact the bovine-based organic material. This is typically done using compost turner vehicles.

FIG. 2C shows the turning of raw bovine-based organic material 206 of FIG. 2B during composting by compost turner 296.

In one embodiment, once the raw bovine-based organic material of operation 203 is aerobically composted at operation 205, process flow proceeds to optional operation 207.

In one embodiment, at optional operation 207 quality control analysis of the composted bovine-based organic material of operation 205 is performed to ensure the desired amounts and types of microbes are present before the composted bovine-based organic material of operation 205 is further processed.

In one embodiment, once quality control analysis of composted bovine-based organic material of operation 205 is performed to ensure the desired amounts and types of microbes are present at operation 207, process flow proceeds to operation 209.

In one embodiment, at operation 209 a first screening of the composted bovine-based organic material of operation 205 is performed to generate first screened initially composted bovine-based organic material.

In one embodiment, the first screening of the composted bovine-based organic material of operation 205 is performed at operation 209 with a one-inch mesh screen.

In addition to screening out over-sized material in the composted bovine-based organic material, the first screening of the composted bovine-based organic material of operation 205 performed at operation 209 further breaks up the composted bovine-based organic material of operation 205 and allows oxygen to make further contact with the composted bovine-based organic material of operation 205, thereby allowing for even better aerobic composting.

In one embodiment, once a first screening of the composted bovine-based organic material of operation 205 is performed at operation 209, process flow proceeds to operation 211.

In one embodiment, at operation 211 the first screened initially composted bovine-based organic material to is allowed settle, and further compost, to generate settled composted bovine-based organic material.

As noted above, in addition to screening out over-sized material in the composted bovine-based organic material, the first screening of the composted bovine-based organic material of operation 205 performed at operation 209 further breaks up the composted bovine-based organic material of operation 205 and allows oxygen to make further contact with the composted bovine-based organic material of operation 205, thereby allowing for even better aerobic composting. Consequently, at operation 211 the composted bovine-based organic material of operation 205 is allowed to settle and further compost before further processing.

In one embodiment, at operation 211 the composted bovine-based organic material of operation 205 is allowed to settle and further compost 5 to 10 days before further processing.

In one embodiment, once the first screened initially composted bovine-based organic material to is allowed settle, and further compost, to generate settled composted bovine-based organic material at operation 211, process flow proceeds to operation 213.

In one embodiment, at operation 213 a screening of the settled composted bovine-based organic material of operation 211 is performed to generate second screened composted bovine-based organic material.

In one embodiment, screening of the settled composted bovine-based organic material of operation 211 is performed at operation 213 with a one-inch mesh screen.

In one embodiment, once a screening of the settled composted bovine-based organic material of operation 211 is performed to generate second screened composted bovine-based organic material at operation 213, process flow proceeds to operation 214.

In one embodiment, at operation 214 an agglomeration system, such as agglomeration system 100 of FIGS. 1A through 1F is provided. Consequently, in one embodiment at operation 214, the agglomeration system provided includes an agglomeration chamber, such as agglomeration chamber 103, with an agglomeration chamber exterior surface, such as agglomeration chamber exterior surface 121, and an agglomeration chamber interior space, such as agglomeration chamber interior space 125, with an agglomeration chamber interior surface, such as agglomeration chamber interior surface 123.

In one embodiment, the agglomeration system provided at operation 214 includes an agglomeration chamber rotational drive system, such as agglomeration chamber rotational drive system 116, for selectively rotating the agglomeration chamber.

In one embodiment, the agglomeration system provided at operation 214 includes an agglomeration chamber misting system, such as agglomeration chamber misting system 106, for selectively providing a mist of water to the interior space of the agglomeration chamber.

In one embodiment, the agglomeration system provided at operation 214 includes an agglomeration system air flow system, such as agglomeration system air flow system 110, for providing air to the agglomeration system.

In one embodiment, the agglomeration system provided at operation 214 includes an agglomeration chamber dryer, such as agglomeration chamber dryer 107, for selectively applying heat to the interior space of the agglomeration chamber.

In one embodiment, the agglomeration system provided at operation 214 includes an agglomeration chamber thermal isolation housing, such as agglomeration chamber thermal isolation housing 101.

In one embodiment, the agglomeration system provided at operation 214 includes an agglomeration chamber thermal isolation housing heating system, such as agglomeration chamber thermal isolation housing heating system 109, for selectively applying heat to the agglomeration chamber thermal isolation housing.

In one embodiment, once an agglomeration system, such as agglomeration system 100 of FIGS. 1A through 1F, is provided at operation 214, process flow proceeds to operation 215.

In one embodiment, at operation 215 the second screened composted bovine-based organic material of operation 213 is provided to the interior space of the agglomeration chamber of operation 214.

FIG. 2D shows the screening of the settled composted bovine-based organic material in bed 297 by screen 298 and providing the second screened composted bovine-based organic material to hopper 105 of the disclosed agglomeration system 100.

In one embodiment, once the second screened composted bovine-based organic material of operation 213 is provided to the interior space of the agglomeration chamber of operation 214 at operation 215, process flow proceeds to operation 217.

In one embodiment, at operation 217 the agglomeration chamber provided at operation 215 is rotated by the agglomeration chamber rotational drive system and a mist of water is provided to the interior space of the agglomeration chamber and the second screened composted bovine-based organic material in the interior space of the agglomeration chamber as the agglomeration chamber is rotated by the agglomeration chamber rotational drive system.

In one embodiment, the agglomeration chamber provided at operation 215 is rotated by the agglomeration chamber rotational drive system at a rate of three to nine rotations per minute as the mist of water is provided to the interior space of agglomeration chamber and the second screened composted bovine-based organic material in the interior space of agglomeration chamber. In one embodiment, the agglomeration chamber provided at operation 215 is rotated by the agglomeration chamber rotational drive system at a rate of six rotations per minute as the mist of water is provided to the interior space of agglomeration chamber and the second screened composted bovine-based organic material in the interior space of agglomeration chamber.

In one embodiment, once the agglomeration chamber provided at operation 215 is rotated by the agglomeration chamber rotational drive system and a mist of water is provided to the interior space of agglomeration chamber and the second screened composted bovine-based organic material in the interior space of agglomeration chamber as the agglomeration chamber is rotated by the agglomeration chamber rotational drive system at operation 217, process flow proceeds to operation 219.

In one embodiment, at operation 219, as the agglomeration chamber provided at operation 215 is rotated by the agglomeration chamber rotational drive system and a mist of water is provided to the interior space of agglomeration chamber and the second screened composted bovine-based organic material in the interior space of agglomeration chamber as the agglomeration chamber is rotated by the agglomeration chamber rotational drive system at operation 217, the agglomeration chamber thermal isolation housing heating system is used to heat the agglomeration chamber thermal isolation housing thermally isolated interior space of the agglomeration chamber thermal isolation housing until the agglomeration chamber interior surface of the agglomeration chamber interior space rises to a desired temperature. The desired temperature of the agglomeration chamber interior surface is then maintained as the agglomeration chamber is rotated by the agglomeration chamber rotational drive system.

In one embodiment, the agglomeration chamber thermal isolation housing heating system is used to heat the agglomeration chamber thermal isolation housing thermally isolated interior space of the agglomeration chamber thermal isolation housing until the agglomeration chamber interior surface of the agglomeration chamber interior space rises to a desired temperature of between eighty and one hundred and twenty degrees Fahrenheit.

In one embodiment, the agglomeration chamber thermal isolation housing heating system is used to heat an agglomeration chamber thermal isolation housing thermally isolated interior space until the agglomeration chamber interior surface of the agglomeration chamber interior space rises to a desired temperature of one hundred degrees Fahrenheit.

The Inventors have discovered that by heating the agglomeration chamber thermal isolation housing thermally isolated interior space until the agglomeration chamber interior surface of the agglomeration chamber interior space rises to a desired temperature, the second screened composted bovine-based organic material in the interior space of agglomeration chamber will not stick or clump to the interior surface of the agglomeration chamber.

In addition, as discussed below, the Inventors have discovered that by simultaneously rotating the agglomeration chamber rotational drive system, misting the interior space of the agglomeration chamber, heating the agglomeration chamber interior surface of the agglomeration chamber interior space and maintaining the desired temperature, the second screened composted bovine-based organic material starts to agglomerate in the interior space of agglomeration chamber into substantially spherical grains with the grain size increasing slowly as the heated agglomeration chamber continues to rotate.

This automatically occurring agglomeration results in grains of composted bovine-based organic material that have a high density of nutrients for a given volume. In addition, it has been discovered by the Inventors that during this agglomeration process the automatically occurring grains of composted bovine-based organic material generate a protective mucus that encases the grains of composted bovine-based organic material.

In one embodiment, once, as the agglomeration chamber provided at operation 215 is rotated by the agglomeration chamber rotational drive system, a mist of water is provided to the interior space of agglomeration chamber and the second screened composted bovine-based organic material in the interior space of agglomeration chamber as the agglomeration chamber is rotated, and the agglomeration chamber thermal isolation housing heating system is used to heat an agglomeration chamber thermal isolation housing thermally isolated interior space until the agglomeration chamber interior surface of the agglomeration chamber interior space rises to a desired temperature, and the agglomeration process begins at operation 219, process flow proceeds to operation 221.

In one embodiment, at operation 221, the agglomeration process begun at operation 219, and the grain size of the second screened composted bovine-based organic material in the interior space of agglomeration chamber as the agglomeration chamber, is monitored.

As noted above, the Inventors have discovered that by simultaneously rotating the agglomeration chamber rotational drive system, misting the interior space of the agglomeration chamber, heating the agglomeration chamber interior surface of the agglomeration chamber interior space and maintaining the desired temperature, the second screened composted bovine-based organic material starts to agglomerate in the interior space of agglomeration chamber into substantially spherical grains with the grain size increasing slowly as the heated agglomeration chamber continues to rotate.

In one embodiment, at operation 221, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the second screened composted bovine-based organic material is being agglomerated, the grain size of the agglomerated bovine-based organic material is monitored.

In one embodiment, the grain size of the agglomerating second screened composted bovine-based organic material is monitored to identify when the average grain size reaches a desired average grain size.

In one embodiment, the desired average grain size of the agglomerated bovine-based organic material is approximately one to five millimeters. In one embodiment, the desired average grain size of the agglomerated bovine-based organic material is approximately two millimeters.

In one embodiment, once the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the second screened composted bovine-based organic material is being agglomerated, and the grain size of the agglomerated bovine-based organic material is monitored at operation 221, process flow proceeds to operation 223.

In one embodiment, at operation 223 when the desired average grain size of the agglomerated bovine-based organic material is achieved, the agglomeration chamber misting system is turned off and the agglomeration chamber dryer is activated to apply heat to the agglomeration chamber interior space and dry the agglomerated bovine-based organic material in the agglomeration chamber interior space.

As noted above, the automatically occurring agglomeration that occurs when the process 200 is performed results in grains of composted bovine-based organic material that have a high density of nutrients for a given volume. In addition, it has been discovered by the Inventors that during this agglomeration process the naturally occurring grains of composted bovine-based organic material generate a protective mucus that encases the grains of composted bovine-based organic material.

In one embodiment, at operation 223, once the desired average grain size is achieved, the agglomerated composted bovine-based organic material is heated to dry the agglomerated composted bovine-based organic material. This process also causes the protective mucus that encases the grains of composted bovine-based organic material to harden, thereby forming a protective coating.

This protective coating has at least two advantages. First the resulting agglomerated bovine-based organic material, with the hardened protective coating, has a shelf life of years. In addition, the resulting agglomerated bovine-based organic material, with the hardened protective coating, has little or no odor since each grain of the resulting agglomerated bovine-based organic material is virtually sealed by the hardened protective coating. This represents a significant improvement over prior art bovine-based organic material.

In one embodiment, once the desired average grain size is achieved and the agglomerated composted bovine-based organic material is heated to dry the agglomerated composted bovine-based organic material at operation 223, process flow proceeds to operation 225.

In one embodiment, at operation 225 the moisture content of the agglomerated bovine-based organic material is monitored as the agglomerated bovine-based organic material is being dried to determine when a desired moisture content has been achieved.

In one embodiment, the desired moisture content is approximately fifteen to thirty percent.

In one embodiment, once the moisture content of the agglomerated bovine-based organic material is being monitored at operation 225, process flow proceeds to operation 227.

In one embodiment, at operation 227, when the desired moisture content of the agglomerated bovine-based organic material is achieved, the agglomeration chamber thermal isolation housing heating system and the agglomeration chamber dryer are turned off. The agglomeration system air flow system is then either maintained on, or turned on, so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, once the desired moisture content of the agglomerated bovine-based organic material is achieved, the agglomeration chamber thermal isolation housing heating system and the agglomeration chamber dryer are turned off, and the agglomeration system air flow system is then either maintained on or turned on so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material at operation 227, process flow proceeds to operation 229.

In one embodiment, at operation 229 a screening of the cooled agglomerated bovine-based organic material is then performed to generate agglomerated bovine-based organic microbial fertilizer.

In one embodiment, the screening of the cooled agglomerated bovine-based organic material is performed using a one quarter inch screen mesh.

FIG. 2E shows one specific example of the agglomerated bovine-based organic microbial fertilizer 299 produced using the process for producing agglomerated organic microbial fertilizer 200 of FIG. 2A in accordance with one embodiment.

In one embodiment, once screening of the cooled agglomerated bovine-based organic material is then performed to generate agglomerated bovine-based organic microbial fertilizer at operation 229, process flow proceeds to optional operation 231.

In one embodiment, at optional operation 231, the agglomerated bovine-based organic microbial fertilizer is further sorted according to grain size.

In this way, different size formulations of the agglomerated bovine-based organic microbial fertilizer can be created and sold for different purposes, such as residential gardening and commercial uses such as golf course fertilization where it is important that the agglomerated bovine-based organic microbial fertilizer have grain sizes small enough to avoid interfering with golf ball rolls and placement.

In one embodiment, once the agglomerated bovine-based organic microbial fertilizer is optionally further sorted according to grain size at optional operation 231, process flow proceeds to operation 233.

In one embodiment, at operation 233, the agglomerated bovine-based organic microbial fertilizer is packaged. As noted above, due to the hardened coating encasing each grain of agglomerated bovine-based organic microbial fertilizer produced using the disclosed methods, the shelf life of the resulting agglomerated bovine-based organic microbial fertilizer is on the order of years. However, to achieve this goal, the agglomerated bovine-based organic microbial fertilizer must be packaged at operation 233 to ensure no exposure to outside moisture.

In one embodiment, once the agglomerated bovine-based organic microbial fertilizer is packaged at operation 233, process flow proceeds to END operation 250 where process 200 is ended.

System

Figure 3:
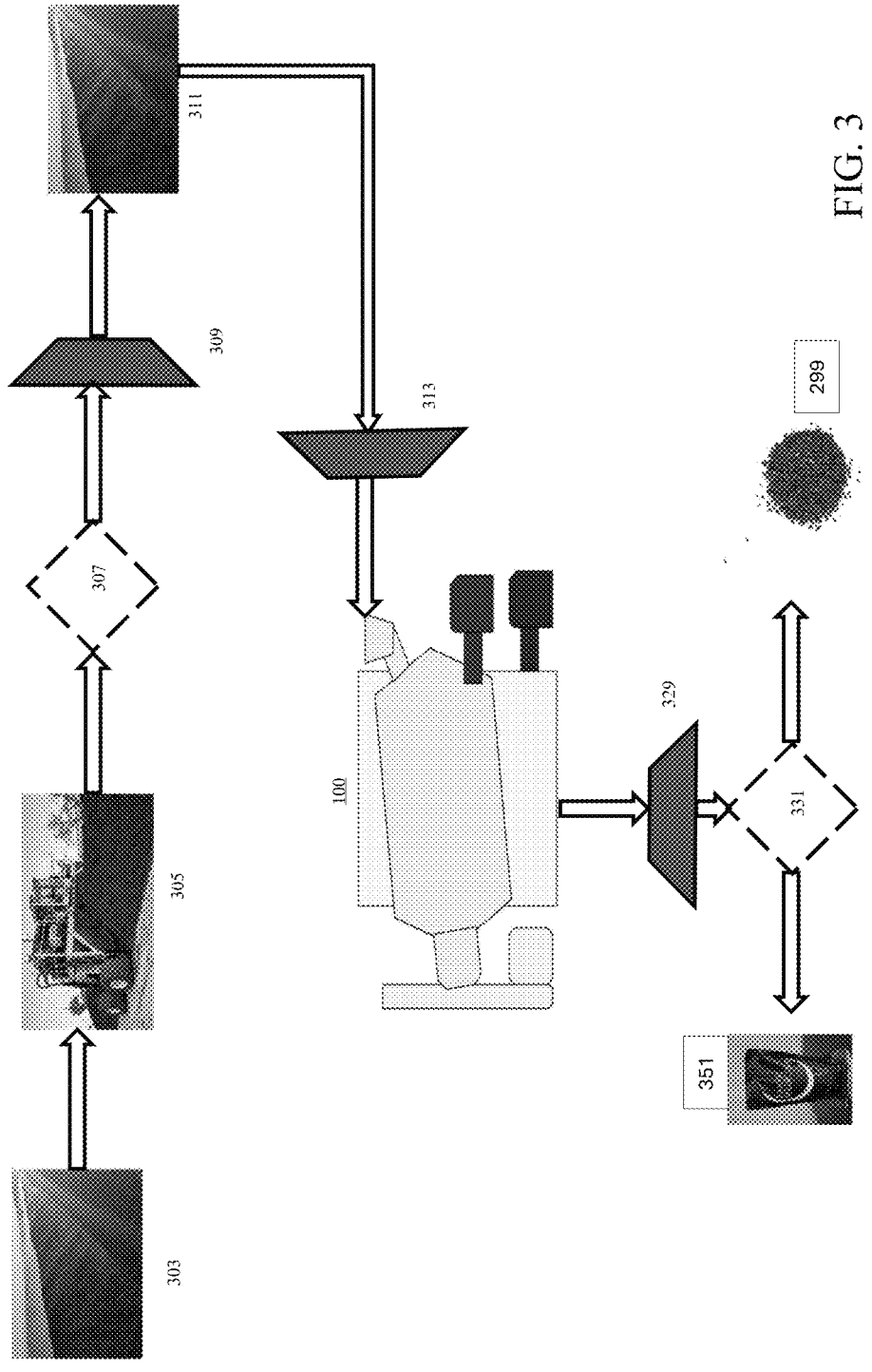
FIG. 3 shows the various components and steps of a system for producing agglomerated organic microbial fertilizer in accordance with one embodiment.

FIG. 3 shows the various components and major operations of a system for producing agglomerated organic microbial fertilizer in accordance with one embodiment.

Referring to FIGS. 1A through 1F, 2A through 2E, and FIG. 3 together, raw bovine-based organic material 303 is obtained.

At 305 initial composting of the raw bovine-based organic material of operation 303 is performed to generate composted bovine-based organic material including the turning of bovine-based organic material.

At 307 quality control analysis of composted bovine-based organic material is performed to ensure the desired amounts and types of microbes are present before the composted bovine-based organic material of is further processed.

Screen 309 is then used to perform a first screening of the composted bovine-based organic material.

Rows 311 of settled first screened initially composted bovine-based organic material are then formed.

Screen 313 is then used to screen the settled composted bovine-based organic material.

Agglomeration system 100 is provided and the second screened composted bovine-based organic material is provided to the interior space of agglomeration chamber where it is agglomerated as described above.

Screen 329 is then used to screen the cooled agglomerated bovine-based organic material to generate agglomerated bovine-based organic microbial fertilizer.

At 331, the agglomerated bovine-based organic microbial fertilizer is further sorted according to grain size to create agglomerated bovine-based organic microbial fertilizer types 351 and 299.

As shown above, the disclosed methods and systems address the shortcomings of the prior art by providing a technical solution to the long-standing technical problem of providing organic microbial fertilizer that has a high density of nutrients per volume, does not have significant odor, has a relatively long shelf-life, can be applied using standard application equipment, and can be processed to accommodate various types of uses including residential and commercial.

To this end, the disclosed methods and systems for providing agglomerated bovine-based organic microbial fertilizer that utilize a novel agglomeration system to produce agglomerated bovine-based organic microbial fertilizer composed of generally spherical granules that have a high density of nutrients per volume, have almost no odor, and have a shelf life of years when properly packaged and stored.

In addition, by controlling the average size of the grains of the agglomerated bovine-based organic microbial fertilizer produced using the disclosed methods and systems, the agglomerated bovine-based organic microbial fertilizer can be sized such that industry standard equipment and spreaders can be used to apply the resulting agglomerated bovine-based organic microbial fertilizer.

In addition, using the disclosed methods and systems, the average size of the grains of the resulting agglomerated bovine-based organic microbial fertilizer can be manipulated to accommodate various types of uses including residential and commercial uses.

Disclosed herein is a method for producing organic microbial fertilizer.

In one embodiment, raw bovine-based organic material is obtained and an initial composting of the raw bovine-based organic material is performed to generate composted bovine-based organic material.

In one embodiment, a first screening of the composted bovine-based organic material is performed to generate first screened initially composted bovine-based organic material.

In one embodiment, the first screened initially composted bovine-based organic material to is allowed settle, and further compost, to generate settled composted bovine-based organic material.

In one embodiment, a screening of the settled composted bovine-based organic material is performed to generate second screened composted bovine-based organic material.

In one embodiment, an agglomeration system is provided. In one embodiment, the agglomeration system includes an agglomeration chamber. In one embodiment, the agglomeration chamber has an agglomeration chamber exterior surface and an agglomeration chamber interior space with an agglomeration chamber interior surface.

In one embodiment, the agglomeration system includes an agglomeration chamber rotational drive system for selectively rotating the agglomeration chamber.

In one embodiment, the agglomeration system includes an agglomeration chamber misting system for selectively providing a mist of water to an interior of the agglomeration chamber.

In one embodiment, the agglomeration system includes an agglomeration system air flow system for providing air to the agglomeration system.

In one embodiment, the agglomeration system includes an agglomeration chamber dryer for selectively applying heat to the interior space of the agglomeration chamber.

In one embodiment, the agglomeration system includes an agglomeration chamber thermal isolation housing. In one embodiment, the agglomeration chamber thermal isolation housing encloses at least a portion of the agglomeration chamber and thereby thermally isolates at least a portion of the agglomeration chamber.

In one embodiment, the agglomeration system includes an agglomeration chamber thermal isolation housing heating system for selectively applying heat to the agglomeration chamber thermal isolation housing.

In one embodiment, the second screened composted bovine-based organic material is provided to the interior space of agglomeration chamber.

In one embodiment, the second screened composted bovine-based organic material in the interior space of agglomeration chamber is agglomerated to generate agglomerated bovine-based organic material.

In one embodiment, the second screened composted bovine-based organic material in the interior space of agglomeration chamber is agglomerated to generate agglomerated bovine-based organic material by using the agglomeration chamber rotational drive system to rotate the agglomeration chamber and the second screened composted bovine-based organic material inside the interior space of agglomeration chamber.

In one embodiment, the second screened composted bovine-based organic material in the interior space of agglomeration chamber is agglomerated to generate agglomerated bovine-based organic material by using the agglomeration chamber misting system to provide a mist of water to the interior space of agglomeration chamber and the second screened composted bovine-based organic material in the interior space of agglomeration chamber as the agglomeration chamber is rotated by the agglomeration chamber rotational drive system.

In one embodiment, the second screened composted bovine-based organic material in the interior space of agglomeration chamber is agglomerated to generate agglomerated bovine-based organic material by using the agglomeration chamber thermal isolation housing heating system to heat an agglomeration chamber thermal isolation housing thermally isolated interior space until the agglomeration chamber interior surface of the agglomeration chamber interior space rises to a desired temperature. The desired temperature of the agglomeration chamber interior surface is then maintained as the agglomeration chamber is rotated by the agglomeration chamber rotational drive system.

In one embodiment, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the second screened composted bovine-based organic material is being agglomerated, the grain size of the agglomerated bovine-based organic material is monitored.

In one embodiment, when a desired average grain size of the agglomerated bovine-based organic material is achieved, the agglomeration chamber misting system is turned off and the agglomeration chamber dryer is activated to apply heat to the agglomeration chamber interior space and dry the agglomerated bovine-based organic material in the agglomeration chamber interior space.

In one embodiment, a moisture content of the agglomerated bovine-based organic material is monitored as the agglomerated bovine-based organic material is being dried.

In one embodiment, when a desired moisture content of the agglomerated bovine-based organic material is achieved, the agglomeration chamber thermal isolation housing heating system and the agglomeration chamber dryer are turned off. The agglomeration system air flow system is then either maintained on or turned on so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, a screening of the cooled agglomerated bovine-based organic material is then performed to generate agglomerated bovine-based organic microbial fertilizer.

In one embodiment, quality control analysis of composted bovine-based organic material is performed before the first screening of the composted bovine-based organic material.

In one embodiment, the agglomerated bovine-based organic microbial fertilizer is further sorted according to grain size.

In one embodiment, the raw bovine-based organic material is dairy cow-based organic material and includes one or more of dairy cow manure, dairy cow pen bedding, and dairy cow feed.

In one embodiment, the first screening of the composted bovine-based organic material to generate first screened initially composted bovine-based organic material is performed with a one-inch mesh screen.

In one embodiment, the second screening of the settled composted bovine-based organic material to generate second screened composted bovine-based organic material is performed with a one-inch mesh screen.

In one embodiment, the agglomeration chamber rotational drive system rotates the agglomeration chamber at approximately 2 to 10 RPM.

In one embodiment, the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is maintained as the agglomeration chamber is rotated by the agglomeration chamber rotational drive system.

In one embodiment, the desired average grain size of the agglomerated bovine-based organic material is approximately 1 to 5 millimeters.

In one embodiment, the desired moisture content of the agglomerated bovine-based organic material is approximately fifteen to thirty percent.

Disclosed herein is a method for producing organic microbial fertilizer.

In one embodiment, the method includes providing composted bovine-based organic material.

In one embodiment, a screening of composted bovine-based organic material is performed to generate screened composted bovine-based organic material.

In one embodiment, an agglomeration system is provided. In one embodiment, the agglomeration system includes an agglomeration chamber. In one embodiment, the agglomeration chamber has an agglomeration chamber exterior surface and an agglomeration chamber interior space with an agglomeration chamber interior surface.

In one embodiment, the agglomeration system includes an agglomeration chamber rotation drive system for selectively rotating the agglomeration chamber.

In one embodiment, the agglomeration system includes an agglomeration chamber misting system for selectively providing a mist of water to an interior of the agglomeration chamber.

In one embodiment, the agglomeration system includes an agglomeration system air flow system for providing air to the agglomeration system.

In one embodiment, the agglomeration system includes an agglomeration chamber dryer for selectively applying heat to the interior space of the agglomeration chamber.

In one embodiment, the agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the agglomeration system includes an agglomeration chamber thermal isolation housing heating system for selectively applying heat to the agglomeration chamber thermal isolation housing.

In one embodiment, the screened composted bovine-based organic material is provided to the interior space of agglomeration chamber.

In one embodiment, the screened composted bovine-based organic material in the interior space of agglomeration chamber is agglomerated to generate agglomerated bovine-based organic material.

In one embodiment, the screened composted bovine-based organic material in the interior space of agglomeration chamber is agglomerated to generate agglomerated bovine-based organic material by using the agglomeration chamber rotational drive system to rotate the agglomeration chamber and the screened composted bovine-based organic material inside the interior space of agglomeration chamber.

In one embodiment, the screened composted bovine-based organic material in the interior space of agglomeration chamber is agglomerated to generate agglomerated bovine-based organic material by using the agglomeration chamber misting system to provide a mist of water to the interior space of agglomeration chamber and the screened composted bovine-based organic material in the interior space of agglomeration chamber as the agglomeration chamber is rotated by the agglomeration chamber rotational drive system.

In one embodiment, the screened composted bovine-based organic material in the interior space of agglomeration chamber is agglomerated to generate agglomerated bovine-based organic material by using the agglomeration chamber thermal isolation housing heating system to heat an agglomeration chamber thermal isolation housing thermally isolated interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system.

In one embodiment, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the screened composted bovine-based organic material is being agglomerated, the grain size of the agglomerated bovine-based organic material is monitored.

In one embodiment, when a desired average grain size of the agglomerated bovine-based organic material is achieved, the agglomeration chamber misting system is turned off and the agglomeration chamber dryer is activated to apply heat to the agglomeration chamber interior space to dry the agglomerated bovine-based organic material in the agglomeration chamber interior space.

In one embodiment, a moisture content of the agglomerated bovine-based organic material is monitored as the agglomerated bovine-based organic material is being dried.

In one embodiment, when a desired moisture content of the agglomerated bovine-based organic material is achieved, the agglomeration chamber thermal isolation housing heating system and the agglomeration chamber dryer are turned off. Then the agglomeration system air flow system either remains on, or is turned on, so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, a screening of the cooled agglomerated bovine-based organic material is performed to generate agglomerated bovine-based organic microbial fertilizer.

In one embodiment, quality control analysis of the composted bovine-based organic material is performed before screening the composted bovine-based organic material.

In one embodiment, the agglomerated bovine-based organic microbial fertilizer is separated according to grain size.

In one embodiment, the composted bovine-based organic material is dairy cow-based composted bovine-based organic material generated from one or more of dairy cow manure, dairy cow pen bedding, and dairy cow feed.

In one embodiment, the screening of the composted bovine-based organic material to generate screened composted bovine-based organic material is performed with a one-inch mesh screen.

In one embodiment, the agglomeration chamber rotational drive system rotates the agglomeration chamber and the screened composted bovine-based organic material at approximately 2 to 10 RPM.

In one embodiment, the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is then maintained as the agglomeration chamber is rotated by the agglomeration chamber rotational drive system.

In one embodiment, the desired average grain size of the agglomerated bovine-based organic material is approximately 1 to 5 millimeters.

In one embodiment, the desired moisture content of the agglomerated bovine-based organic material is approximately fifteen to thirty percent.

Disclosed herein is a method for producing organic microbial fertilizer.

In one embodiment, raw bovine-based organic material is obtained.

In one embodiment, an initial composting of the raw bovine-based organic material is performed to generate composted bovine-based organic material.

In one embodiment, a first screening of the composted bovine-based organic material is performed to generate first screened initially composted bovine-based organic material using a one-inch mesh screen.

In one embodiment, the first screened initially composted bovine-based organic material is allowed to settle to generate settled composted bovine-based organic material.

In one embodiment, a screening of the settled composted bovine-based organic material is performed to generate second screened composted bovine-based organic material using a one-inch mesh screen.

In one embodiment, an agglomeration system is provided. In one embodiment, the agglomeration system includes an agglomeration chamber, the agglomeration chamber having an agglomeration chamber exterior surface and an agglomeration chamber interior space with an agglomeration chamber interior surface.

In one embodiment, the agglomeration system includes an agglomeration chamber rotational drive system for selectively rotating the agglomeration chamber.

In one embodiment, the agglomeration system includes an agglomeration chamber misting system for selectively providing a mist of water to an interior of the agglomeration chamber.

In one embodiment, the agglomeration system includes an agglomeration system air flow system for providing air to the agglomeration system.

In one embodiment, the agglomeration system includes an agglomeration chamber dryer for selective applying heat to the interior space of the agglomeration chamber.

In one embodiment, the agglomeration system includes an agglomeration chamber thermal isolation housing. In one embodiment, the agglomeration chamber thermal isolation housing encloses at least a portion of the agglomeration chamber and thereby thermally isolates at least a portion of the agglomeration chamber.

In one embodiment, the agglomeration system includes an agglomeration chamber thermal isolation housing heating system for selectively applying heat to the agglomeration chamber thermal isolation housing.

In one embodiment, the second screened composted bovine-based organic material is provided to the interior space of agglomeration chamber.

In one embodiment, the second screened composted bovine-based organic material in the interior space of agglomeration chamber is agglomerated to generate agglomerated bovine-based organic material.

In one embodiment, the second screened composted bovine-based organic material in the interior space of agglomeration chamber is agglomerated to generate agglomerated bovine-based organic material by using the agglomeration chamber rotational drive system to rotate the agglomeration chamber and the second screened composted bovine-based organic material inside the interior space of agglomeration chamber at approximately 2 to 10 RPM.

In one embodiment, the second screened composted bovine-based organic material in the interior space of agglomeration chamber is agglomerated to generate agglomerated bovine-based organic material by using the agglomeration chamber misting system to provide a mist of water to the interior space of agglomeration chamber and the second screened composted bovine-based organic material in the interior space of agglomeration chamber as the agglomeration chamber is rotated by the agglomeration chamber rotational drive system at approximately 2 to 10 RPM.

In one embodiment, the second screened composted bovine-based organic material in the interior space of agglomeration chamber is agglomerated to generate agglomerated bovine-based organic material by using the agglomeration chamber thermal isolation housing heating system to heat an agglomeration chamber thermal isolation housing thermally isolated interior space until the agglomeration chamber interior surface of the agglomeration chamber interior space rises to a desired temperature of approximately 80 to 120 degrees Fahrenheit and to maintain the agglomeration chamber interior surface at the desired temperature of approximately 80 to 120 degrees Fahrenheit as the agglomeration chamber is rotated by the agglomeration chamber rotational drive system at approximately 2 to 10 RPM.

In one embodiment, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the second screened composted bovine-based organic material is being agglomerated, the grain size of the agglomerated bovine-based organic material is monitored.

In one embodiment, when a desired average grain size of 2 to 5 millimeters of the agglomerated bovine-based organic material is achieved, the agglomeration chamber misting system is turned off. Then the agglomeration chamber dryer is activated to apply heat to the agglomeration chamber interior space and dry the agglomerated bovine-based organic material in the agglomeration chamber interior space.

In one embodiment, a moisture content of the agglomerated bovine-based organic material is monitored as the agglomerated bovine-based organic material is being dried.

In one embodiment, when a desired moisture content of fifteen to thirty percent for the agglomerated bovine-based organic material is achieved, the agglomeration chamber thermal isolation housing heating system and the agglomeration chamber dryer are turned off. Then the agglomeration system air flow system is either left on, or is turned on, so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, a screening of the cooled agglomerated bovine-based organic material is performed to generate agglomerated bovine-based organic microbial fertilizer.

Disclosed herein is a system for producing organic microbial fertilizer.

In one embodiment, the system includes composted bovine-based organic material.

In one embodiment, the system includes a screening system for screening the composted bovine-based organic material to generate screened composted bovine-based organic material.

In one embodiment, the system includes an agglomeration system. In one embodiment, the agglomeration system includes an agglomeration chamber, the agglomeration chamber having an agglomeration chamber exterior surface and an agglomeration chamber interior space with an agglomeration chamber interior surface.

In one embodiment, the agglomeration system includes an agglomeration chamber rotation drive system for selectively rotating the agglomeration chamber.

In one embodiment, the agglomeration system includes an agglomeration chamber misting system for selectively providing a mist of water to the interior space of the agglomeration chamber.

In one embodiment, the agglomeration system includes an agglomeration system air flow system for providing air to the agglomeration system.

In one embodiment, the agglomeration system includes an agglomeration chamber dryer for selectively applying heat to the interior space of the agglomeration chamber.

In one embodiment, the agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the agglomeration system includes an agglomeration chamber thermal isolation housing heating system for selectively applying heat to the agglomeration chamber thermal isolation housing, wherein the screened composted bovine-based organic material is provided to the interior space of agglomeration chamber.

In one embodiment, the agglomeration system is used to agglomerate the screened composted bovine-based organic material in the interior space of agglomeration chamber to generate agglomerated bovine-based organic material by using the agglomeration chamber rotational drive system to rotate the agglomeration chamber and the screened composted bovine-based organic material inside the interior space of agglomeration chamber.

In one embodiment, the agglomeration system is used to agglomerate the screened composted bovine-based organic material in the interior space of agglomeration chamber to generate agglomerated bovine-based organic material by using the agglomeration chamber misting system to provide a mist of water to the interior space of agglomeration chamber and the screened composted bovine-based organic material in the interior space of agglomeration chamber as the agglomeration chamber is rotated by the agglomeration chamber rotational drive system.

In one embodiment, the agglomeration system is used to agglomerate the screened composted bovine-based organic material in the interior space of agglomeration chamber to generate agglomerated bovine-based organic material by using the agglomeration chamber thermal isolation housing heating system to heat an agglomeration chamber thermal isolation housing thermally isolated interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system.

In one embodiment, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the screened composted bovine-based organic material is being agglomerated, monitoring the grain size of the agglomerated bovine-based organic material.

In one embodiment, when a desired average grain size of the agglomerated bovine-based organic material is achieved, turning off the agglomeration chamber misting system and activating the agglomeration chamber dryer to apply heat to the agglomeration chamber interior space and the agglomerated bovine-based organic material in the agglomeration chamber interior space.

In one embodiment, a moisture content of the agglomerated bovine-based organic material is monitored as the agglomerated bovine-based organic material is being dried.

In one embodiment, when a desired moisture content of the agglomerated bovine-based organic material is achieved, turning off the agglomeration chamber thermal isolation housing heating system and the agglomeration chamber dryer. In one embodiment, then leaving on, or turning on, the agglomeration system air flow system so that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

In one embodiment, the composted bovine-based organic material is dairy cow-based composted bovine-based organic material generated from one or more of dairy cow manure, dairy cow pen bedding, and dairy cow feed.

In one embodiment, the screening system includes a screen with a one-inch mesh.

In one embodiment, the agglomeration chamber drive system rotates the agglomeration chamber and the screened composted bovine-based organic material at approximately 2 to 10 RPM.

In one embodiment, the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is maintained as the agglomeration chamber is rotated by the agglomeration chamber rotational drive system.

In one embodiment, the desired average grain size of the agglomerated bovine-based organic material is approximately 1 to 5 millimeters.

In one embodiment, the desired moisture content of the agglomerated bovine-based organic material is approximately fifteen to thirty percent.

Disclosed herein is a composted organic material agglomeration system. In one embodiment, the composted organic material agglomeration system includes an agglomeration chamber, the agglomeration chamber having an agglomeration chamber exterior surface and an agglomeration chamber interior space with an agglomeration chamber interior surface.

In one embodiment, the composted organic material agglomeration system includes an agglomeration chamber rotation drive system for selectively rotating the agglomeration chamber.

In one embodiment, the composted organic material agglomeration system includes an agglomeration chamber misting system for selectively providing a mist of water to the interior space of the agglomeration chamber.

In one embodiment, the composted organic material agglomeration system includes an agglomeration system air flow system for providing air to the agglomeration system.

In one embodiment, the composted organic material agglomeration system includes an agglomeration chamber dryer for selective applying heat to the interior space of the agglomeration chamber.

In one embodiment, the composted organic material agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the composted organic material agglomeration system includes an agglomeration chamber thermal isolation housing heating system for selectively applying heat to the agglomeration chamber thermal isolation housing, wherein the screened composted organic material to the interior space of agglomeration chamber.

In one embodiment, the agglomeration system is used to agglomerate composted organic material in the interior space of agglomeration chamber to generate agglomerated organic material by using the agglomeration chamber rotational drive system to rotate the agglomeration chamber and composted organic material inside the interior space of agglomeration chamber.

In one embodiment, the agglomeration system is used to agglomerate composted organic material in the interior space of agglomeration chamber to generate agglomerated organic material by using the agglomeration chamber misting system to provide a mist of water to the interior space of agglomeration chamber and the composted organic material in the interior space of agglomeration chamber as the agglomeration chamber is rotated by the agglomeration chamber rotational drive system.

In one embodiment, the agglomeration system is used to agglomerate composted organic material in the interior space of agglomeration chamber to generate agglomerated organic material by using the agglomeration chamber thermal isolation housing heating system to heat an agglomeration chamber thermal isolation housing thermally isolated interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system.

In one embodiment, as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the composted organic material is being agglomerated, monitoring the grain size of the agglomerated organic material.

In one embodiment, when a desired average grain size of the agglomerated organic material is achieved, the agglomeration chamber misting system is turned off and the agglomeration chamber dryer is activated to apply heat to the agglomeration chamber interior space and dry the agglomerated organic material in the agglomeration chamber interior space.

In one embodiment, when a desired moisture content of the agglomerated organic material is achieved, the agglomeration chamber thermal isolation housing heating system and the agglomeration chamber dryer are turned off and the agglomeration system air flow system is left on, or turned on, such that the agglomeration chamber and the agglomerated organic material in the agglomeration chamber interior space is rotated by the agglomeration chamber rotational drive system while being cooled by the agglomeration system air flow system to generate cooled agglomerated organic material.

In one embodiment, the composted organic material is dairy cow-based composted organic material generated from one or more of dairy cow manure, dairy cow pen bedding, and dairy cow feed.

In one embodiment, the screening system includes a screen with a one-inch mesh.

In one embodiment, the agglomeration chamber drive system rotates the agglomeration chamber and the screened composted organic material at approximately 2 to 10 RPM.

In one embodiment, the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is maintained as the agglomeration chamber is rotated by the agglomeration chamber rotational drive system.

In one embodiment, the desired average grain size of the agglomerated organic material is approximately 1 to 5 millimeters.

In one embodiment, the desired moisture content of the agglomerated organic material is approximately fifteen to thirty percent.

Disclosed herein is a composted organic material agglomeration system. In one embodiment, the composted organic material agglomeration system includes an agglomeration chamber, the agglomeration chamber having an agglomeration chamber exterior surface and an agglomeration chamber interior space with an agglomeration chamber interior surface.

In one embodiment, the composted organic material agglomeration system includes an agglomeration chamber rotational drive system for selectively rotating the agglomeration chamber.

In one embodiment, the composted organic material agglomeration system includes an agglomeration chamber misting system for selectively providing a mist of water to the interior space of the agglomeration chamber.

In one embodiment, the composted organic material agglomeration system includes an agglomeration system air flow system for providing air to the agglomeration system.

In one embodiment, the composted organic material agglomeration system includes an agglomeration chamber dryer for selective applying heat to the interior space of the agglomeration chamber.

In one embodiment, the composted organic material agglomeration system includes an agglomeration chamber thermal isolation housing, the agglomeration chamber thermal isolation housing enclosing at least a portion of the agglomeration chamber and thereby thermally isolating at least a portion of the agglomeration chamber.

In one embodiment, the composted organic material agglomeration system includes an agglomeration chamber thermal isolation housing heating system for selectively applying heat to the agglomeration chamber thermal isolation housing.

It should be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In the discussion above, certain aspects of one embodiment include process steps and/or operations described herein for illustrative purposes in a particular order and/or grouping. However, the particular order and/or grouping shown and discussed herein are illustrative only and not limiting. Those of skill in the art will recognize that other orders and/or grouping of the process steps and/or operations are possible and, in some embodiments, one or more of the process steps and/or operations discussed above can be combined and/or deleted. In addition, sections of one or more of the process steps and/or operations can be re-grouped as sections of one or more other of the process steps and/or operations discussed herein. Consequently, the particular order and/or grouping of the process steps and/or operations discussed herein do not limit the scope of the invention as claimed below.

In addition, the features shown in the figures are identified using a particular nomenclature for ease of description and understanding, but other nomenclature is often used in the art to identify equivalent features.

Therefore, numerous variations, whether explicitly provided for by the specification or implied by the specification or not, may be implemented by one of skill in the art in view of this disclosure.

What is claimed is:

1. A system for producing organic microbial fertilizer comprising:

composted bovine-based organic material;

a screening system for screening the composted bovine-based organic material to generate screened composted bovine-based organic material;

an agglomeration system including:

an agglomeration chamber, the agglomeration chamber having an agglomeration chamber exterior surface and an agglomeration chamber interior space with an agglomeration chamber interior surface;

an agglomeration chamber rotation drive system for selectively rotating the agglomeration chamber;

an agglomeration chamber misting system for selectively providing a mist of water to the interior space of the agglomeration chamber;

an agglomeration system air flow system for providing air to the agglomeration system;

an agglomeration chamber dryer for selectively applying heat to the interior space of the agglomeration chamber;

an agglomeration chamber thermal isolation housing, the agglomeration chamber thermal isolation housing enclosing at least a portion of the agglomeration chamber and thereby thermally isolating at least a portion of the agglomeration chamber;

an agglomeration chamber thermal isolation housing heating system for selectively applying heat to the agglomeration chamber thermal isolation housing, wherein the screened composted bovine-based organic material is provided to the interior space of agglomeration chamber;

wherein the agglomeration system is used to agglomerate the screened composted bovine-based organic material in the interior space of the agglomeration chamber to generate agglomerated bovine-based organic material by:

using the agglomeration chamber rotational drive system to rotate the agglomeration chamber and the screened composted bovine-based organic material inside the interior space of the agglomeration chamber;

using the agglomeration chamber misting system to provide a mist of water to the interior space of the agglomeration chamber and the screened composted bovine-based organic material in the interior space of agglomeration chamber as the agglomeration chamber is rotated by the agglomeration chamber rotational drive system;

using the agglomeration chamber thermal isolation housing heating system to heat an agglomeration chamber thermal isolation housing thermally isolated interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system;

as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the screened composted bovine-based organic material is being agglomerated, monitoring the grain size of the agglomerated bovine-based organic material;

when a desired average grain size of the agglomerated bovine-based organic material is achieved, turning off the agglomeration chamber misting system and activating the agglomeration chamber dryer to apply heat to the agglomeration chamber interior space and the agglomerated bovine-based organic material in the agglomeration chamber interior space;

monitoring a moisture content of the agglomerated bovine-based organic material as the agglomerated bovine-based organic material is being dried;

when a desired moisture content of the agglomerated bovine-based organic material is achieved, turning off the agglomeration chamber thermal isolation housing heating system and the agglomeration chamber dryer and turning on the agglomeration system air flow system such that the agglomeration chamber and the agglomerated bovine-based organic material in the agglomeration chamber interior space is rotated by the agglomeration chamber rotational drive system while being cooled by the agglomeration system air flow system to generate cooled agglomerated bovine-based organic material.

2. The system of claim 1, wherein the composted bovine-based organic material is dairy cow-based composted bovine-based organic material generated from one or more of dairy cow manure, dairy cow pen bedding, and dairy cow feed.

3. The system of claim 1, wherein the screening system includes a screen with a one-inch mesh.

4. The system of claim 1, wherein the agglomeration chamber drive system rotates the agglomeration chamber and the screened composted bovine-based organic material at approximately 2 to 10 RPM.

5. The system of claim 1, wherein the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is maintained as the agglomeration chamber is rotated by the agglomeration chamber rotational drive system.

6. The system of claim 1, wherein the desired average grain size of the agglomerated bovine-based organic material is approximately 1 to 5 millimeters.

7. The system of claim 1, wherein the desired moisture content of the agglomerated bovine-based organic material is approximately 15 to 30%.

8. A composted organic material agglomeration system including:

an agglomeration chamber, the agglomeration chamber having an agglomeration chamber exterior surface and an agglomeration chamber interior space with an agglomeration chamber interior surface;

an agglomeration chamber rotation drive system for selectively rotating the agglomeration chamber;

an agglomeration chamber misting system for selectively providing a mist of water to the interior space of the agglomeration chamber;

an agglomeration system air flow system for providing air to the agglomeration system;

an agglomeration chamber dryer for selective applying heat to the interior space of the agglomeration chamber;

an agglomeration chamber thermal isolation housing, the agglomeration chamber thermal isolation housing enclosing at least a portion of the agglomeration chamber and thereby thermally isolating at least a portion of the agglomeration chamber;

an agglomeration chamber thermal isolation housing heating system for selectively applying heat to the agglomeration chamber thermal isolation housing, wherein composted organic material is provided to the interior space of the agglomeration chamber;

wherein the agglomeration system is used to agglomerate composted organic material in the interior space of the agglomeration chamber to generate agglomerated organic material by:

using the agglomeration chamber rotational drive system to rotate the agglomeration chamber and composted organic material inside the interior space of the agglomeration chamber;

using the agglomeration chamber misting system to provide a mist of water to the interior space of the agglomeration chamber and the composted organic material in the interior space of the agglomeration chamber as the agglomeration chamber is rotated by the agglomeration chamber rotational drive system;

using the agglomeration chamber thermal isolation housing heating system to heat an agglomeration chamber thermal isolation housing thermally isolated interior space until the agglomeration chamber interior surface of the agglomeration chamber interior space rises to a desired temperature and to maintain the desired temperature of the agglomeration chamber interior surface as the agglomeration chamber is rotated by the agglomeration chamber rotational drive system;

as the agglomeration chamber is concurrently rotated by the agglomeration chamber rotational drive system, misted by the agglomeration chamber misting system, the agglomeration chamber interior surface of the agglomeration chamber interior space is maintained at the desired temperature, and the composted organic material is being agglomerated, monitoring the grain size of the agglomerated organic material;

when a desired average grain size of the agglomerated organic material is achieved, turning off the agglomeration chamber misting system and activating the agglomeration chamber dryer to apply heat to the agglomeration chamber interior space and dry the agglomerated organic material in the agglomeration chamber interior space; and when a desired moisture content of the agglomerated organic material is achieved, turning off the agglomeration chamber thermal isolation housing heating system and the agglomeration chamber dryer and turning on the agglomeration system air flow system such that the agglomeration chamber and the agglomerated organic material in the agglomeration chamber interior space is rotated by the agglomeration chamber rotational drive system while being cooled by the agglomeration system air flow system to generate cooled agglomerated organic material.

9. The system of claim 8, wherein the composted organic material is dairy cow-based composted organic material generated from one or more of dairy cow manure, dairy cow pen bedding, and dairy cow feed.

10. The system of claim 8, wherein the screening system includes a screen with a one-inch mesh.

11. The system of claim 8, wherein the agglomeration chamber drive system rotates the agglomeration chamber and the composted organic material at approximately 2 to 10 RPM.

12. The system of claim 8, wherein the agglomeration chamber thermal isolation housing heating system is used to heat the agglomeration chamber thermal isolation housing thermally isolated interior space until the agglomeration chamber interior surface of the agglomeration chamber interior space rises to a desired temperature of 80 to 120 degrees Fahrenheit which is maintained as the agglomeration chamber is rotated by the agglomeration chamber rotational drive system.

13. The system of claim 8, wherein the desired average grain size of the agglomerated organic material is approximately 1 to 5 millimeters.

14. The system of claim 8, wherein the desired moisture content of the agglomerated organic material is approximately 15 to 30%.

15. A composted organic material agglomeration system including:

an agglomeration chamber, the agglomeration chamber having an agglomeration chamber exterior surface and an agglomeration chamber interior space with an agglomeration chamber interior surface;

an agglomeration chamber rotational drive system for selectively rotating the agglomeration chamber;

an agglomeration chamber misting system for selectively providing a mist of water to the interior space of the agglomeration chamber;

an agglomeration system air flow system for providing air to the agglomeration system;

an agglomeration chamber dryer for selective applying heat to the interior space of the agglomeration chamber;

an agglomeration chamber thermal isolation housing, the agglomeration chamber thermal isolation housing enclosing at least a portion of the agglomeration chamber and thereby thermally isolating at least a portion of the agglomeration chamber;

an agglomeration chamber thermal isolation housing heating system for selectively applying heat to the agglomeration chamber thermal isolation housing.

\* \* \* \* \*